United States Patent
Chekanovskaya (12)

(10) Patent No.: US 6,274,146 B1
(45) Date of Patent: Aug. 14, 2001

(54) BIOLOGICALLY ACTIVE PHYTOGENOUS PROTEOGLYCAN AND A METHOD OF MAKING THEREOF

(76) Inventor: Ludmila Chekanovskaya, ul, Tallinskaya, D 5, Korp. 2, Kv. 47, Moscow 12345 (RU)

( * ) Notice: Subject to any disclaimer, the term of this patent is extended or adjusted under 35 U.S.C. 154(b) by 0 days.

(21) Appl. No.: 09/529,752

(22) Filed: Apr. 17, 2000

(30) Foreign Application Priority Data

Oct. 20, 1999 (RU) ................................. 99121933

(51) Int. Cl.$^7$ .................. A61K 35/78; C07K 1/100; C07K 14/00; C07K 17/00
(52) U.S. Cl. ................ 424/195.1; 530/395; 514/931; 514/934
(58) Field of Search ................ 424/195.1, 725; 514/931, 934; 530/395

(56) References Cited

U.S. PATENT DOCUMENTS 5,711,948 * 1/1998 Pospelova et al. .

\* cited by examiner

Primary Examiner—Leon B. Lankford, Jr.
Assistant Examiner—Michele Flood
(74) Attorney, Agent, or Firm—I.. Zborovsky

(57) ABSTRACT

A biologically active phytogenous proteoglycan not having hemagglutinating activity via water solution obtained by disintegration of divisible plant cells from young potato plants, *Solanum tuberosum* of the Family Solanaceae, fractionated and concentrated to obtain a dry substance with a molecular mass of $8.0 \times 10^5 - 2.5 \times 10^6$D and the mass percentages of the following elements: nitrogen 1.12–2.48%, carbon 39.93–44.42%, hydrogen 5.15–7.21%; the remaining is an ash component, which includes a polysaccharide chain consisting of residues of neutral sugars in the amount of 34.0–85.3% and in the following mass percentages: glucose 26.4–33.1%, galacturonic acid 19.0–25.1%, arabinose 1.7–4.4%, uronic acids 12.0–18.0%, rhamnose 1.2–10.0%, xylose 0.1–3.0%, mannose 0.1–5.0%, galactose 2.5–27.0%; and up to 15 ng of pro that consists of amino acids residues in the following quantities based on ng per 0.1 mg of proteoglycan: asparagine 126.0–146.0 ng, serine 139.0–159.0 ng, glutamine 263.0–283.0 ng, glycine 117.0–131.0 ng, alanine 80.0–100.0 ng, valine 76.0–96.0 ng, leucine 85.0–105.0 ng, lysine 62.0–85.0 ng, arginine 42.0–62.0 ng; and trace amounts of cysteine, isoleucine, histidine, phenylalanine, tyrosine, and threonine.

4 Claims, No Drawings

BIOLOGICALLY ACTIVE PHYTOGENOUS PROTEOGLYCAN AND A METHOD OF MAKING THEREOF

BACKGROUND OF THE INVENTION

The invention refers to biologically active substances and, in particular, to phytogenous proteoglycans applied in medicine, pharmacology, veterinary medicine, and biology as a component of medicinal products.

Yeast glucan is known that increases resistance in experimental animals to bacterial, fungal, viral, and parasitic infections. For example, Browder et al. have shown in Int. Immunopharm, 1984, 6, #1 pp. 19–26, that the administering of yeast glucan before intravenous contamination of *Staphilococcus aureus* mice resulted in almost double increase in infected animal lifetime. On a model of gram-negative bacterial sepsis the peritoneal injection of yeasty glucan considerably reduced system bacteremia and increased animals survival rate as was shown by D. L. Williams, et al (J. Reticuloendothelial Soc., 1978, V. 23, pp. 479–490). The same authors demonstrated the efficiency of glucan with viral hepatitis in mice. Glucan administration supported Kupfer's cell phagocyte activity, promoting thereby regeneration of hepatocytes However, with application of yeast glucan the formation of granulomas in liver and the development of allergic diseases was observed.

Bioactive polysaccharide γ-PL (gamma-plant) is also known, which is extracted from plant cells, for example from corn, potato, marine fungus, etc. With the molecular mass equal to $2 \times 10^6 \pm 9 \times 10^5 D$ and element composition (mass %) as follows: nitrogen 1.7–1.98; carbon 40.12–40.39; hydrogen 5.81–6.07; the remainder is the ash component which includes the polysaccharide chain consisting of (mass %) neutral carbohydrate residues (35.0–41.0), glucose (27.0–33.0), galacturonic acid (19.0–25.0), arabinose (1.7–2.3), uronic acids (12.0–18.0) and protein (no less than 0.5) that consists of amino acids residues in the following quantities (per 0.1 g of ⊖-pl): asparagin 126.0–146.0, serine 139.0–159.0, glutamine 263.0–283.0, glycine 117.0–131.0, alanine 80.0–100.0, valine 76.0–96.0, leucine 85.0–105.0, lysine 65.0–85.0, arginine 42.0–62.0; in trace quantities are: cystein, isoleucine, histidine, phenylalanine, tyrosine, threonine. As an anti-infective agent gPL was studied during treatment of viral and bacterial infections in laboratory and agricultural animals. With experimental infection of mice by viruses of simple herpes such as 1 and 2 types on the model of herpetic meningocephalitis at application of a dose $10LD_{50}gPL$ protective effect reached 60%. Comparatively narrow range of anti-infective activity as well as an occurrences of local inflammatory reactions while subcutaneous injections are gPL applications shortcomings.

SUMMARY OF THE INVENTION

It is therefore an object of the present invention to eliminate the shortcomings mentioned above by creation of a new substance having a broad spectrum of anti-infectious activities and free from side effects.

In keeping with these objects and with others which will become apparent hereinafter, one feature of the present invention is to provide a substance which is the gPL—new biologically active phytogenous proteoglycan obtained by disintegration of divisible plant cells, for example, from young potato (*Solanum tuberosum*, family Solanacae) plants via water solution. More particularly, in accordance with the present invention, a new biologically active phytogenous proteoglycan is provided, which includes a biologically active phytogenous proteoglycan and not developing hemagglutinating activity and obtained by disintegration of divisible plant cells, for example, from young potato (*Solanum tuberosum*, family Solanancae) plants via water solution, fractionated and concentrated to obtain a substance with a molecular mass of $8.0 \times 10^5 – 2.5 \times 10^6 D$ and the following composition (mass %): nitrogen 1.12–2.48; carbon 39.93–44.42; hydrogen 5.15–7.21; the remaining is the ash component which includes the polysaceharide chain consisting of (mass %) residues of neutral sugars (34.0–85.3), glucose (26.4–33.1), galacturonic acid (19.0–25.1), arabinose (1.7–4.4), uronic acids (12.0–18.0), ramnose (1.2–10.0), xylose (0.1–3.0), mannose (0.1–5.0), galactose (2.5–27.0), and protein (up to 15.0) that consists of amino acids residues in the following quantities (ng per 0.1 mg of proteoglycan): asparagin 126.0–146.0, serine 139.0–159.0, glutamine 263.0–283.0, glycine 117.0–131.0, alanine 80.0–100.0, valine 76.0–96.0, leucine 85.0–105.0, lysine 65.0–85.0, arginine 42.0–62.0; in trace quantities there are: cystein, isoleucine, histidine, phenylalanine, tyrosine, threonine.

In accordance with another feature of present invention, a method for producing a biologically active proteoglycan which is proposed which includes the steps of shredding into mush-like condition a raw material in from germinated potato bulbs *Solanum tuberosum*, Solanacae family extracting with boiling water (with water: material rate 1.1:1.2), holding for 23÷25 h at 20° C., separating by filtration of an extract obtained into a solid and a liquid phase, fractionating the latter by means of either gel-chromatography or filtration to remove fractions with a molecular weight not exceeding $8.0 \times 10^5 D$, concentrating the extract obtained to an end-product in form of a dry powder.

The novel features which are considered as characteristic for the present invention are set forth in particular in the appended claims.

DESCRIPTION OF PREFERRED EMBODIMENTS

In accordance with the present invention, a substance is proposed which is the gPL—new biologically active phytogenous proteoglycan obtained by disintegration of divisible plant cells, for example, from young potato (*Solanum tuberosum*, family Solanacae) plants via water solution fractionated in and concentrated to obtain a dry substance with a molecular mass $8.0 \times 10^5 – 2.5 \times 10^6 D$, and with composition (mass %) is as follows: nitrogen 1.12–2.48; carbon 39.93–44.42; hydrogen 5.15–7.21; the remaining is the ash component which includes the polysaccharide chain consisting of (mass %) residues of neutral sugars (34.0–85.3), glucose (26.4–33.1), galacturonic acid (19.0–25.1), arabinose (1.7–4.4), uronic acids (12.0–18.0), ramnose (1.2–10.0), xylose (0.1–3.0), mannose (0.1–5.0), galactose (2.5–27.0), and protein (up to 15.0) that consists of amino acids residues in the following quantities (ng per 0.1 mg of proteoglycan): asparagin 126.0–146.0, serine 139.0–159.0, glutamine 263.0–283.0, glycine 117.0–131.0, alanine 80.0–100.0, valine 76.0–96.0, leucine 85.0–105.0, lysine 65.0–85.0, arginine 42.0–62.0; a trace quantities that are: cystein, isoleucine, histidine, phenylalanine, tyrosine, threonine. Proteoglycan is characterized by the following infrared spectrum peaks (KBr tablet): 3350, 2920, 1270, 1655, 1620, 1610, 1560, 1510, 1405, 1378, 1296, 1145, 1080, 1040, 920, 842, 763 $cm^{-1}$. The substance in question is insoluble in organic solvents and soluble in aqueous and saline solvents, possesses anti-infectious properties and does not possess hemagglutinating properties.

Proteoglycan element composition is distinct from that of gamma-plant due to the fact that, apart from monosaccharides, which are present in gamma-plant, it contains ramnose, xylose, mannose, and galactose and has a wide anti-infectious spectrum.

A method of producing the new proteoglycan is described hereinbelow.

The method involves raw material shredding, extraction by water, keeping at the temperature of 20° C. within 24 hours, extract separation and, finally, concentrating to a dry substance. In accordance with the invention, young root plants of potato Solanum tuberosum (Solanaseae family) bulbs are used as raw material. The process of extraction is carried out with boiling water or water having PH value in the limits of 4,5–6,5. The extract obtained is fractionated and concentrated to molecular mass to remove low molecule fractions with the weight not exceeding $8.0 \times 10^5 D$.

The method will be realized in the following way: roots that growing out from eyelets in potato bulbs are used as a raw material. Thus, the end-product is obtained from "awakening plant", i.e. from the part of a plant, the growth of which is the most active and, hence, this part contains a great deal of biologically active substances, which can manifest the highest ant;l-infectious properties. The raw material, preferably, is to be shredded into mush-like mass that is necessary to optimize extracting as well as to gain maximum activity of the plant source. Any disperser may be used for this purpose as a homogenizer. The shredded product is extracted with boiling water in correlation "water: plant hemogenate" from 1:1 to 1:2 and is kept for 24 h at 20° C.

The extract, obtained according to the method claimed, is separated by filtration into liquid and solid phase. For any filtration step a press, similar to these used for extract production, may be applied.

During the incubation that follows, the extract is fractionated according to the molecular mass; the main purpose of the action is to exclude fractions with low molecular mass (less than $8 \times 10^5 D$), i.e. by means of both gel-chromatography or filtration. Such carriers as Sephadex G-200 or higher of Sepharose type (the commercial products manufactured by Pharmacia Fine Chemicals AB company, Sweden), or others with similar characteristics or others with the similar characteristics. The carrier separates the extract into two components: one, containing fractions with molecular masses less than $8 \times 10^5 D$ and the other with fractions with molecular masses more than $8 \times 10^5 D$. The first one is to be disposed of.

The ultrafiltration process is carried out by means of membranes such as PM-10 (the commercial product manufactured by American Corp., USA) or with hemodyalisis cartridge such as H120 (the commercial product manufactured by B. Brown Melsungen AG, Germany), Fresensius F-40, -60, -80 and other (the commercial product manufactured by MTS Medizine Technische Systeme GMBH, German) or finally with 23-08 model (the commercial product manufactured by Baxer Healthcare Corp., USA). Then the product with the required molecular weight is brought to the concentration needed (for example, by vacuum evaporation, ultrafiltration, or by any other means available).

The final stage of the method is dry substance obtaining, for example, by means of lyophilization, i.e. vacuum evaporation at a low temperature or precipitation in ethanol presence, or by any other method.

The isolated amorphous light-grey odorless powder is a high-molecular proteoglycan of phytogenous derivation easily soluble both in water and water solutions (for example, 9% NaCl or glucose solution), and insoluble in ethanol methanol, chlorophorm, ether, or acetone. The active basis of the substance contains the following monosaccharides (%): residues of neutral sugars (34.0–85.3), glucose (26.4–33.1), galacturonic acid (19.0–25.1), arabinose (1.7–4.4), uronic acids (12.0–18.0), ramnose (1.2–10.0), xylose (0.1–3.0), mannose (0.1–5.0), galactose (2.5–27.0), and protein (up to 15.0) that consists of amino acids residues in the following quantities (ng per 0.1 mg of proteoglycan): asparagin 126.0–146.0, serine 139.0–159.0, glutamine 263.0–283.0, glycine 117.0–131.0, alanine 80.0–100.00, valine 76.0–96.0, leucine 85.0–105.0, lysine 65.0 85.0, arginine 42.0–62.0 ;in trace quantities there are: cystein, isoleucine, histidine, phenylalanine, tyrosine, threonine. Proteoglycan is characterized by the following infra-red spectrum peaks (KBr tablet): 3350, 2920, 1720, 1655, 1620, 1610, 1560, 1510, 1405, 1378, 1296, 1145, 1080, 1040, 920, 842, 763 cm$^1$.

The inventive proteoglycan is insoluble in organic solvents and soluble in aqueous and saline solvents. It possesses antiviral, antibacterial and antimycotic activities and does not manifest hemagglutinating activity. The molecular mass of the proteoglycan is equal to $8 \times 10^5 D$ and its elemental composition (mass %) is as follows: nitrogen 1.12–2.48; carbon 39.93–44.42; hydrogen 5.15–7.21; the remaining is the ash component. The melting point could not be determined since the substance decomposes at temperature 273° C. The refraction factor of 5% solution is equal to 1.338±0.005.

The examples of experiments on proteoglycan biological activity are given below.

EXAMPLES

Proteoglycan biological activity both protective and therapeutic were estimated using various models in animals infected artificially, animals infected in natural way, and in human volunteers. In all cases mentioned above comparison with the drugs that are known was performed.

Experiment 1

Proteoglycan efficiency was estimated by means of herpetic menigeoencephalitis model in mice. The 1-st type of simple virus herpes of Kleiman strained was used. The virus infectuous titer in Vero cells culture was of 6.5–7.01 1 g $CPA_{50}^{1}/0.1$ ml while by intracerebral or intraperitonneal introduction in white mice mass of 7–8 g it was equal to 5.5–6.0 1 g $LD_{50}/0.03$ ml. The strain is characterized by increased neurovirulence. The maximum lesion of cells of fibroblasts in hen embryons or of Vero cells (75–100%) was already observed in 18–20 h after infecting. To reproduce herpetic meningoencephalitis in mice the latter were infected with Kleiman virus intraperitonneally in volume of 0.2 ml of both 10 and 100 $LD_{50}$ doses. The treatment results were estimated as a mean lifespan (ML) and the protective effect which is difference between survival rates in experimental and control groups. Proteoglycan efficiency when herpetic meningoencephalitis model in mice (30 animals in each group) is shown in the table below:

| Way of application | Survival rate (%) | Lethality rate (%) | Protective effect (%) | ML (days) |
|---|---|---|---|---|
| 10 $LD_{50}$ virus dose | | | | |
| A* | 80 | 20 | 63 | 13.2 ± 1.9 |
| B** | 70 | 30 | 53 | 11.8 ± 1.6 |
| Control group | 17 | 83 | | 4.2 ± 1.2 |
| Acyclovir group | 32 | 68 | 15 | 7.81 ± 1.9 |
| 100 $LD_{50}$ virus dose | | | | |
| A* | 57 | 43 | 57 | 9.6 ± 2.9 |
| B** | 63 | 37 | 63 | 10.6 ± 1.8 |
| Control group | 0 | 100 | 0 | 3.3 ± 1.2 |
| Acyclovir group | 0 | 100 | 0 | 5.3 ± 1.8 |

*-proteoglycan was introduced 5 days before infecting
**-proteoglycan was introduced 5 days until infecting and 3 h after the infecting.
** Acyclovir was introduced in 3, 24, 48, 72 and 96 h after the infecting. Proteoglycan application for herpetic meningoencephalits in mice resulted in either more expressed preventive or therapeutical action in comparison with the control and acyclovir groups. 10 $LD_{50}$ virus dose proteoglycan which protective effect 53–63%, in comparison with acyclovir—15%; and with 100 $LD_{50}$ the protective effect reached 57–63% while in acyclovir case no effect was observed.

Experiment 2

As a parvoviral infection model, dogs of English beagle breed were taken. Eight individuals were included in both control and experimental group. Parvoviral enteritis was confirmed by clinical and laboratory investigations. In blood swabs of infected animals expressed leukopenia was observed. The amounts of leukocytes was reduced to 50% of the normal while erythrocytes' amount was normal. The control group of animals was treated in conventional way which was aimed, primarily, at elimination of vomiting, dehydration, acidosis, and secondary infections. The animals of the group, selected from the same brood, got only proteoglycan, according to the following scheme: 6 dogs got one shot daily subcutaneously for 2 days and 2 dogs got one shot intravenously. All animals of the control group died, and the autopsy provided the diagnosis previously given. In experimental group all individuals have recovered and obvious signs of improving in clinical state of ill dogs were already observed on the day following the beginning of therapy.

Experiment 3

Proteoglycan was used for treatment of cytomegalovirus (CMV) infection in ring-tailed lemurs (*Lemur catta*) in zoo. CMV presence in lemurs was diagnosed with highly specific methods, i.e. both with immunoenzyme and immunofluorescence analysis. These allow to identify the interaction between specific monoclonal antibodies and group-specific antigens of CMVI viruses. To diagnose the presence of antibodies against CMVI, vaccinal strain Ad 169 (the most sensitive to a wide spectrum of antibodies against CMVI) was used. The outbreak among lemurs was accompanied by mass mortality because of an acute coronary-respiratory failure. Among the clinical signs a general limpness and a loss of appetite are worth to be noted. Such a state went on for about two weeks and resulted in death, The cadaveric material was used to diagnose as well as blood samples from peripheral (ulnar) veins of live lemurs. Diagnosis of CMVI antigens was performed before and after proteoglycan treatment. The preparation was introduced in 11 lemurs two times in two weeks period.

| Animal | Females | | | | | Males | | | Cubs | | |
|---|---|---|---|---|---|---|---|---|---|---|---|
| Animal number | 3 | 2 | 16 | 25 | 29 | 5 | 18 | 27 | 1 | 2 | 3 |
| 1* | +++ | ++ | 16 | 25 | – | – | – | 27 | ++ | – | 3 |
|  |  | + |  |  |  |  |  |  | + |  |  |
| 2* | – | – | – | – | – | – | – | – | – | – | – |

CMVI antigen presence before (*) and after (**) proteoglycan treatment. The symbols +, ++, and +++ signify the amount of viruses in animals. The data above manifest that the proteoglycan treatment resulted in the complete recovery of all animals diseased.

Experiment 4

Mice (C57B1/6xCBA)F, line with a mass 18–20 g were infected artificially with *Salmonella typhimurium* microbial mass, strain 415. In each group there were 10 animals. Proteoglycan was introduced 5 days prior to contamination. The efficacy of the preparation was estimated as % of animals survived. The survival rate was estimated during 1–24 days after contamination.

| Animal group | Survival rate (%) at 0.5 $LD_{50}$ infection dose | Survival rate (%) at 2.0 $LD_{50}$ infection dose |
|---|---|---|
| Experimental groups | 100 | 90 |
| Control group | 30 | 0 |

With 2.0 $LD_{50}$ contamination does mass animal mortality was observed during 5–6 days after the contamination. When the preparation administration took place, mass mortality was not observed; losses of individual animals were distributed evenly within observation period. In this case, the preparation protective effect was up to 70% with the dose of 0.5 $LD_{50}$ and 90% with the dose 2.0 $LD_{50}$.

Acute and chronic toxicity of the new phytogenous proteoglycan were studied in accordance with the following official documents.
1. Requirements to the clinical tests for new pharmacologic compounds (The State Committee of Pharmacology of the Ministry of Health). Russia, Moscow, 1992.
2. Estimation of mutagenicity of new drugs. (The State Committee of Pharmacology of the Ministry of Health) Moscow, Russia, 1992.
3. Guidelines for experimental and clinical studies of new drugs. (The State Committee of Pharmacology of the Ministry of Health). Moscow, Russia, 1985.

As a result of profound studies of proteoglycan acute and chronic toxicity with various ways of introduction (intravenous, subcutaneous, etc.) in various animal species (dogs, rabbits, Guinea pigs, rats, mice) insignificant toxicity of the proteoglycan was shown. Judging by the data concerning the basic vital indices and the quantitative toxicity characteristics, the maximum tolerance dose administered subcutaneously in mice was equal to 4350 mg/kg while in rats it was equal to 5980 mg/kg ($LD_{50-2650}$ mg/kg and 2940 mg/kg respectively).

When administered intravenously, the maximum tolerance dose for rats was 4580 mg/kg while the $LD_{50}$ dose was equal to 2750 mg/kg.

While acute and chronic toxicity tests proteoglycan did not suppress hemopoiesis and did not cause any sufficient changes of peripheral blood characteristics, i did not affect most of metabolism in animal blood serum (protein, carbohydrates and mineral metabolisms, amino transferase activity etc.). Both therapeutic and average doses of the preparation did not cause toxic effect on liver. Proteoglycan does not manifest mutagenous, embryotoic, or teratogenic effects. The results of estimation of toxicogenic and allergenic activities were negative.

Proteoglycan in a dried up form is stable, well kept (when packed) at +4° C., is not hygroscopic. It is well soluble in water solvents. Proteoglycan biological activity in the form of sterile solution remains unchanged for 7 years.

The preparation may be used in the form of solution for injecting in any way—endolymphic, intravenous, sucutaneous, intraperitoneal etc., as well as in the form of suppositories for vaginal and rectal applications, and also as aerosols, drops and other drug forms.

Experiment 5

Proteoglycan therapeutic efficiency was estimated in comparison with that of conventional therapy of patients suffering from acute and chronic gastrointestinal diseases associated with Helicobacter pylori. 116 volunteers of both sexes with clinical signs of an appropriate disease were busy in the experiment. Proteoglycan therapeutic efficiency was estimated according to the clinical protocol scheduled in advance. Patients' ages were from 23 to 57 years. Disease duration varied from a few weeks to some years. Comparison group involved 39 persons. The preparation was applied in the form of sterile 9% sodium chloride solution. The object of study in the case given were scrapes taken from mucosa of various stomach portions in the patients who suffered from gastric ulcer and chronic gastritis.

Histological, gistochemical, and bacterioscopic preparations obtained for the scrapes for morphologic and bacterioscopic investigations made these more objective. Patients with confirmed Helicobacter pylori presence on the mucous membrane of gastrointestinal tract were selected from proteoglycan treatment. After proteoglycan was administered, repeatedly taken scrapes were tested.

Antihelicobacterial action was revealed in 95% of patients. At the same time Helicobacter pylori elimination positive clinical effect was revealed that was expressed as pain syndrome reduction and amplification of repair process in stomach mucosa. No side effects were observed as a result of proteoglycan application.

A group of patients with both acute and chronic gastrooenteric diseases accompanied with disbacteriosis and funcgous diseases were observed. In intestinal microflora studies it was revealed that in all cases of hepatitis (21 patients) there are disorders in intestinal microbiocenosis: the amount of lactobacteria was reduced in 100% cases, the amount of bifidum bacteria was reduced in 82% cases,—and the same refers to of *Esherichia coil* (71.4%). With obligate microflora reduction in 75% patients *enterococcus* was revealed, while in 50% examined patients yeast fungus was observed. Virology test of feces revealed both presence of rotaviral antigen in 3 (13.6 5) patients and adenoviral antigen in 6 (27.2%) patients. Improvements in intestines microbiocenosis in patients treated with proteoglycan for 14–21 and more observation days were shown in comparison with the controls. Increasing of lactobacteria amount was manifested in 15% patients, while for bifidum bacteria it amounted to 11%. Yeast fungi were found out in 28% patients only. In two patients the complete elimination of fungi *Candida albicans* after the treatment was observed.

Examination for viral antigens after proteoglycan treatment proved disappearance of rota—and adenoviral antigens in native material.

Experiments described above are only the illuminative examples of anti-infectious action of proteoglycan claimed. These do not exhaust completely a broad range of infectious antigens which this substrate is able to eliminate Evidently, insignificant toxicity and high biological activity allow to look forward its' application in human and animal medicine, pharacology, and biology as an active drug component.

It will be understood that each of the elements described above, or two or more together, may also find a useful application in other types of substances differing from the types described above.

While the invention has been illustrated and described as embodied in biologically active phytogenous proteoglycan and method of its obtaining, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

What is claimed is:

1. A biologically active phytogenous proteoglycan not having hemagglutinating activity via water solution obtained by disintegration of divisible plant cells from young potato plants, Solanum tuberosum of the Family Solanaceae, fractionated and concentrated to obtain a dry substance with a molecular mass of $8.0 \times 10^5$–$2.5 \times 10^6$ D and the mass percentages of the following elements: nitrogen 1.12–2.48%, carbon 39.93–44.42%, hydrogen 5.15–7.21%; the remaining is an ash component, which includes a polysaccharide chain consisting of residues of neutral sugars in the amount of 34.0–85.3% and in the following mass percentages: glucose 26.4–33.1%, galacturonic acid 19.0–25.1%, arabinose 1.7–4.4%, uronic acids 12.0–18.0%, rhamnose 1.2–10.0%, xylose 0.1–3.0%, mannose 0.1–5.0%, galactose 2.5–27.0%; and up to 15 ng of that consists of amino acids residues in the following quantities based on ng per 0.1 mg of proteoglycan: asparagine 126.0–146.0 ng, serine 139.0–159.0 ng, glutamine 263.0–283.0 ng, glycine 117.0–131.0 ng, alanine 80.0–100.0 ng, valine 76.0–96.0 ng, leucine 85.0–105.0 ng, lysine 62.0–85.0 ng, arginine 42.0–62.0 ng; and trace amounts of cysteine, isoleucine, histidine, phenylalanine, tyrosine, and threonine.

2. A biologically active phytogenous proteoglycan as defined in claim 1, which has the following infra-red spectrum peaks (KBr tablet): 3350, 2920, 1720, 1655, 1610, 1560, 1405, 1378, 1296, 1145, 1080, 1040, 920, 842, and 736 $cm^{-1}$.

3. A biologically active phytogenous proteoglycan as defined in claim 1, which is insoluble in organic solvents, soluble in saline solvents and water, has antiviral activity against DNA- and RNA- containing viruses, antibacterial activity against Mycoplasma and Chlamydia, and antimycotic activity, and does not exhibit hemagglutinating activity.

4. A method of producing biologically active a phytogenous proteoglycan comprising the steps of shredding into mush-like condition a raw material from germinated potato bulbs of *Solanum tuberosum* of the Family Solanaceae, extracting with boiling water, whereby the ratio of the water to the raw material is 1.1:1.2, separating by filtration an extract into a solid and a liquid phase, fractionating the latter by either gel-chromatography or filtration to remove fractions with a molecular weight not exceeding $8.0 \times 10^5 D$, concentrating the extract to obtain a dry powder.

* * * * *